US011433135B2

(12) United States Patent
Grant et al.

(10) Patent No.: US 11,433,135 B2
(45) **Date of Patent: *Sep. 6, 2022**

(54) HIGH CAPACITY DIKETOPIPERAZINE MICROPARTICLES AND METHODS

(71) Applicant: MannKind Corporation, Westlake Village, CA (US)

(72) Inventors: Marshall Grant, Newtown, CT (US); Paul Menkin, Branford, CT (US); Grayson W. Stowell, Cary, NC (US)

(73) Assignee: MannKind Corporation, Westlake Village, CA (US)

( * ) Notice: Subject to any disclaimer, the term of this patent is extended or adjusted under 35 U.S.C. 154(b) by 379 days.

This patent is subject to a terminal disclaimer.

(21) Appl. No.: 16/739,506

(22) Filed: Jan. 10, 2020

(65) Prior Publication Data

US 2020/0147221 A1 May 14, 2020

Related U.S. Application Data

(60) Continuation of application No. 16/453,826, filed on Jun. 26, 2019, now Pat. No. 10,603,383, which is a continuation of application No. 16/151,678, filed on Oct. 4, 2018, now Pat. No. 10,376,587, which is a division of application No. 15/152,355, filed on May 11, 2016, now Pat. No. 10,130,709, which is a division of application No. 14/127,158, filed as application No. PCT/US2012/042998 on Jun. 18, 2012, now Pat. No. 9,364,436.

(60) Provisional application No. 61/498,476, filed on Jun. 17, 2011.

(51) Int. Cl.

| | |
|---|---|
| *A61K 47/22* | (2006.01) |
| *A61K 9/00* | (2006.01) |
| *A61K 9/14* | (2006.01) |
| *A61K 38/28* | (2006.01) |
| *A61K 9/50* | (2006.01) |

(52) U.S. Cl.

CPC ............ *A61K 47/22* (2013.01); *A61K 9/0075* (2013.01); *A61K 9/14* (2013.01); *A61K 9/50* (2013.01); *A61K 38/28* (2013.01); *Y10T 428/2982* (2015.01)

(58) Field of Classification Search

CPC ........ A61K 47/22; A61K 9/0075; A61K 9/14; A61K 9/50; A61K 38/28; Y10T 428/2982

See application file for complete search history.

*Primary Examiner* — Genevieve S Alley

(74) *Attorney, Agent, or Firm* — Withers Bergman LLP; Alan D. Gardner

(57) ABSTRACT

Disclosed herein are diketopiperazine microparticles having high capacity for adsorbing a drug or active agent. In particular, the diketopiperazine microparticle are formed using fumaryl diketopiperazine and can comprise a drug in large doses for the treatment of disease or disorders by pulmonary delivery via oral inhalation.

16 Claims, 6 Drawing Sheets

FIG. 1A
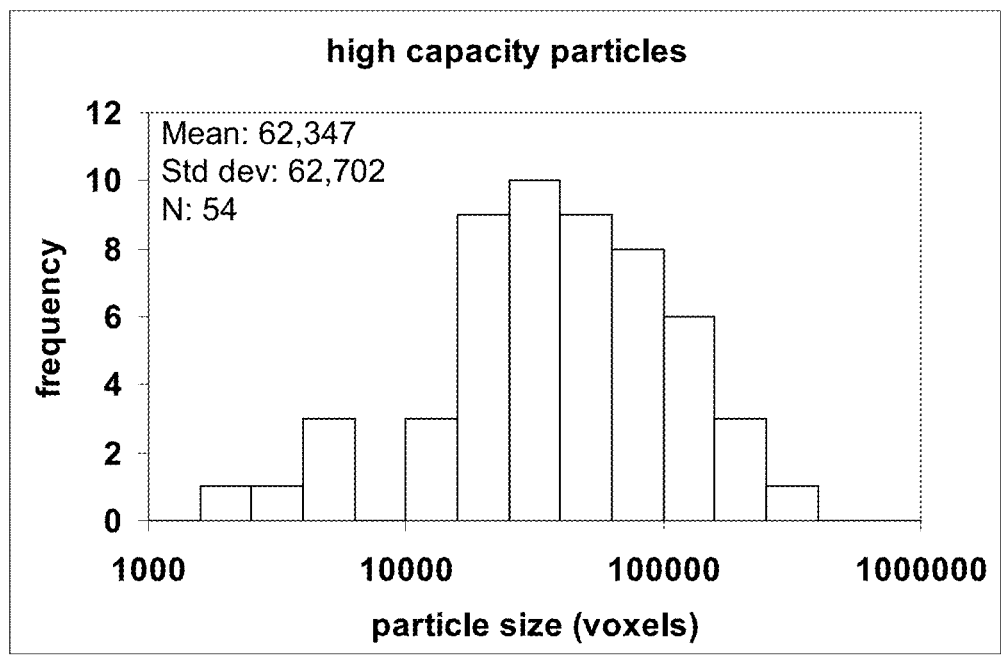
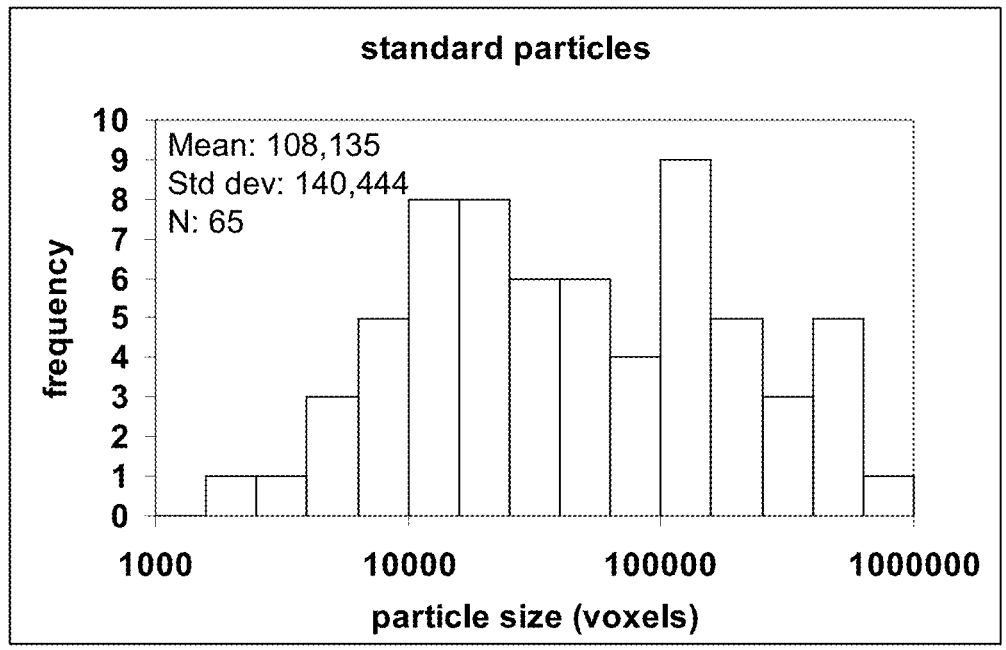
FIG. 1B

FIG. 2A
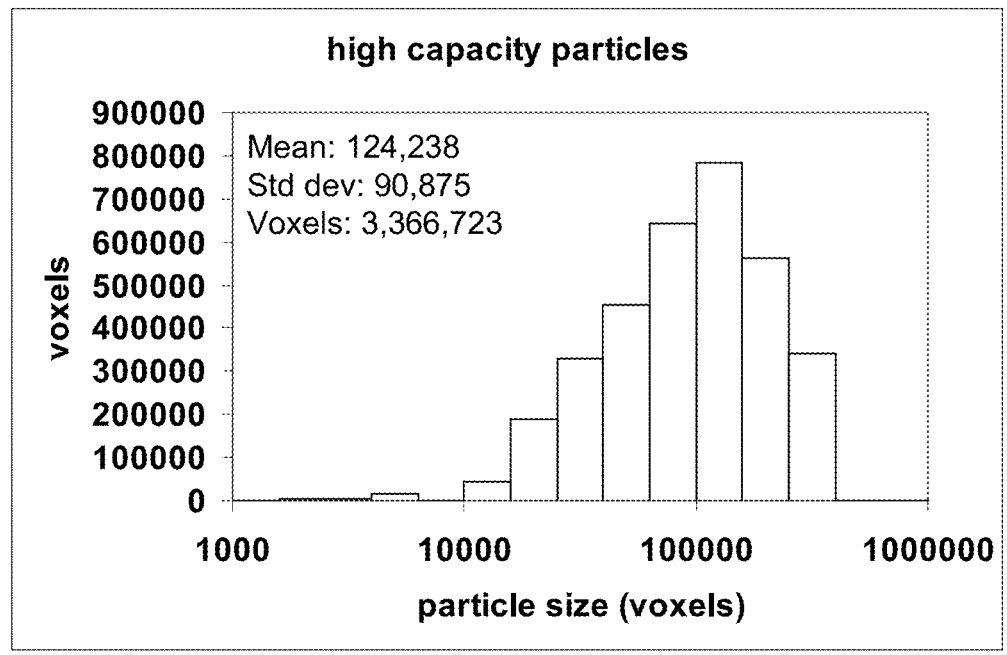
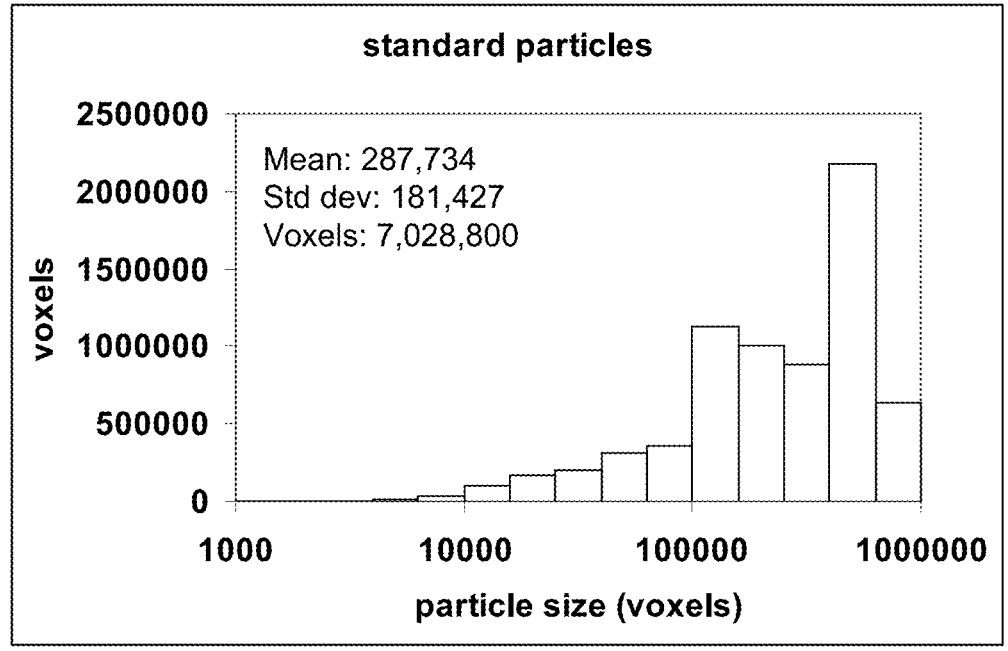
FIG. 2B

FIG. 3A
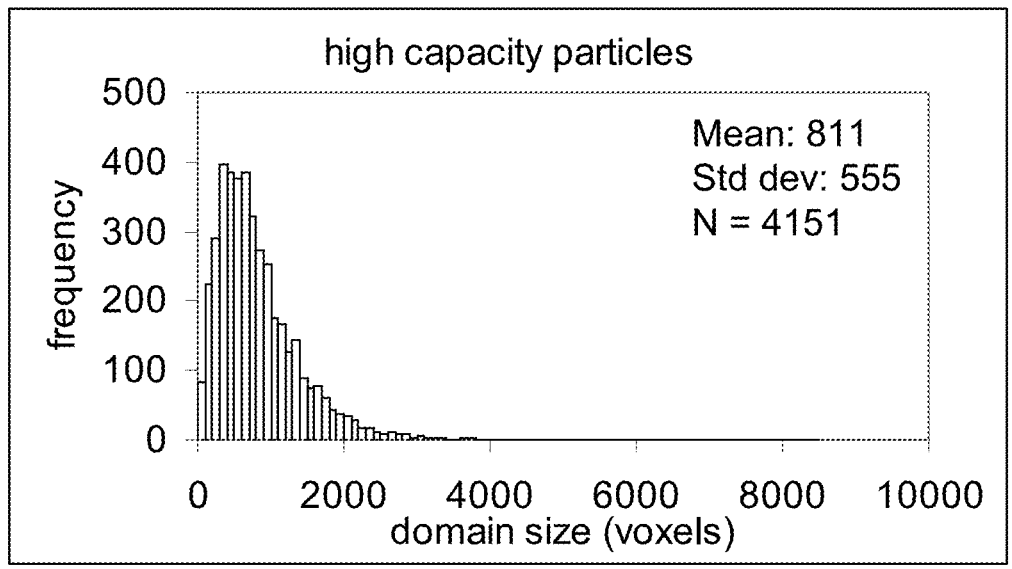
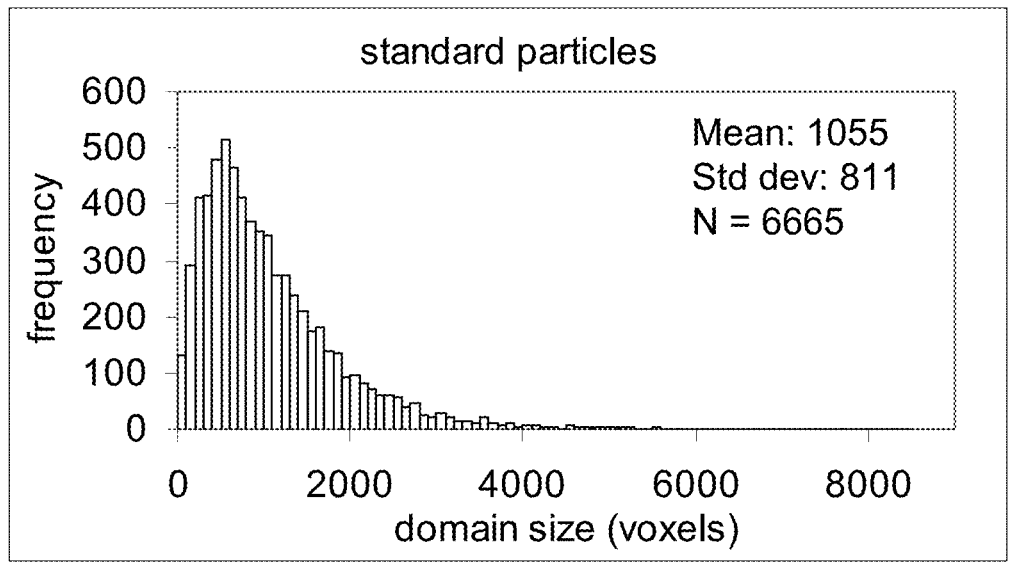
FIG. 3B

FIG. 4A
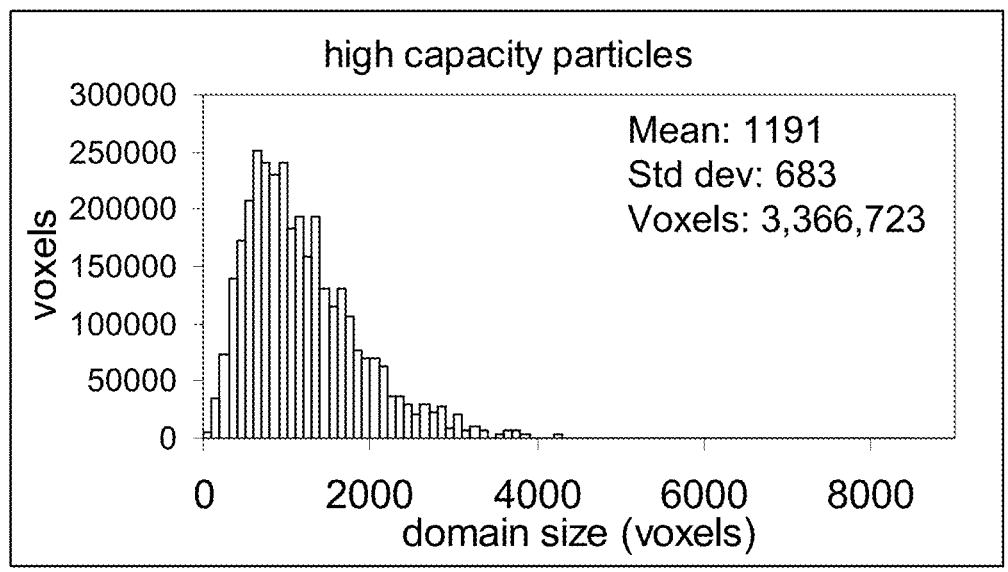
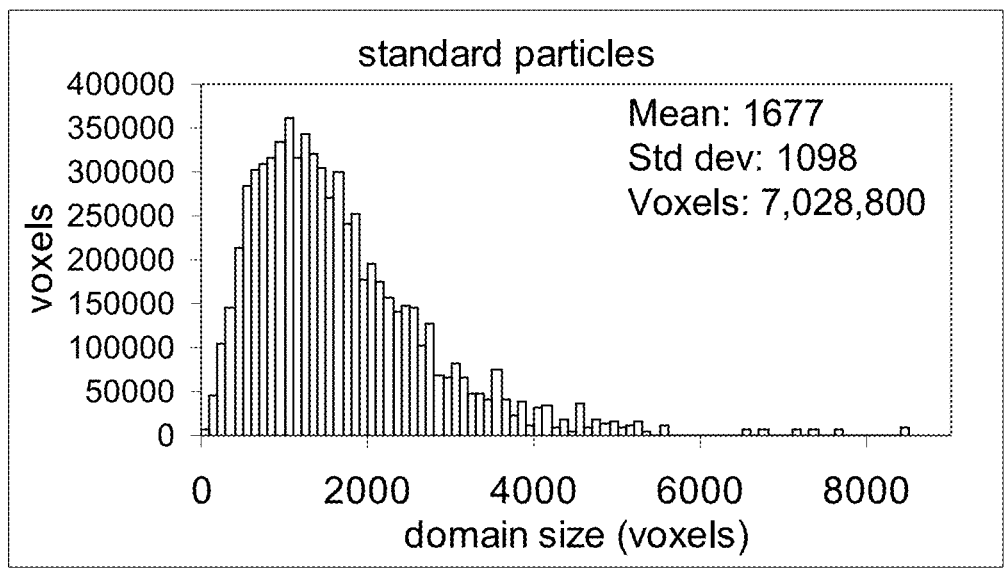
FIG. 4B

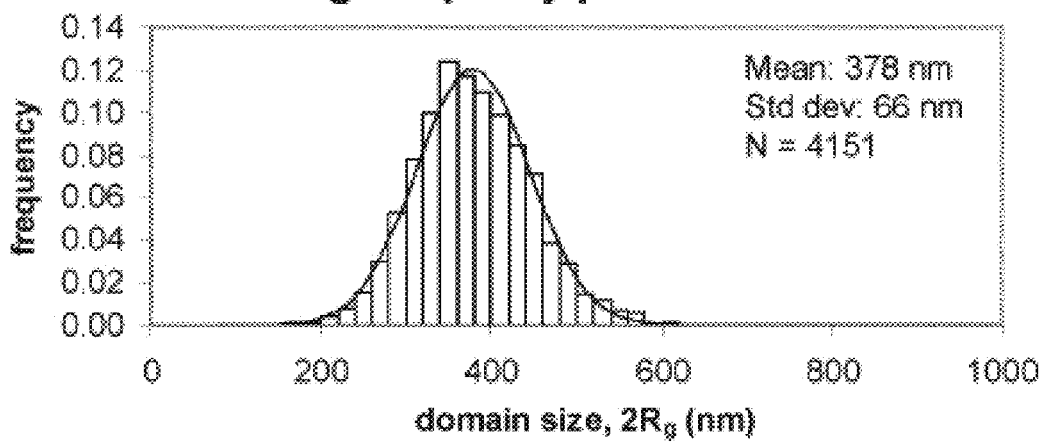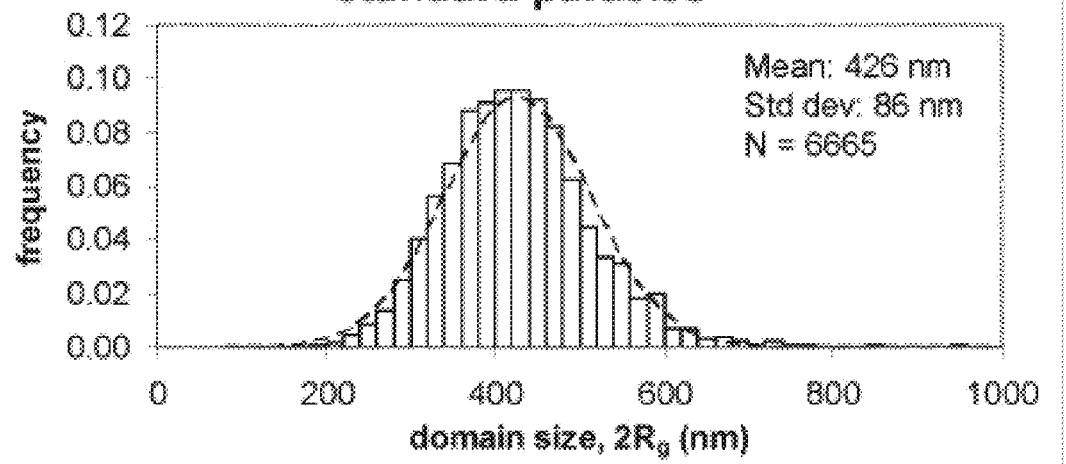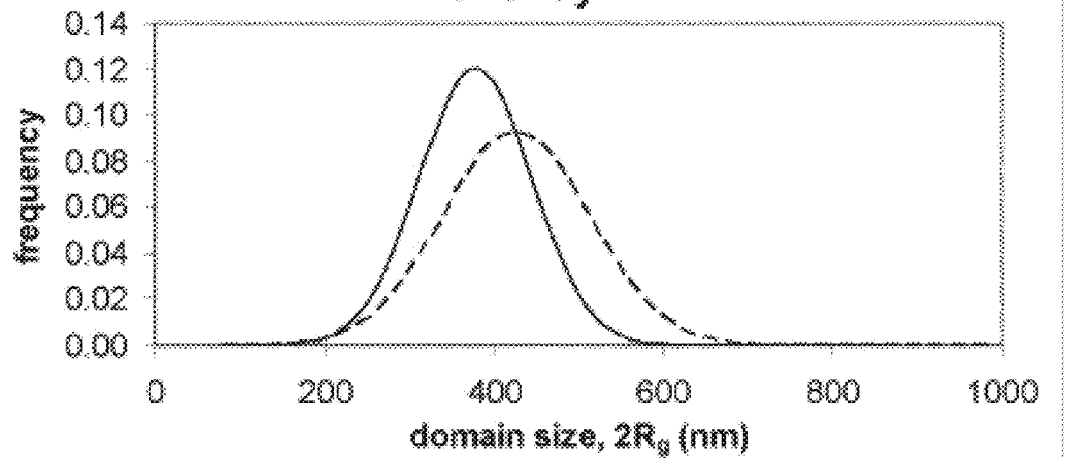

HIGH CAPACITY DIKETOPIPERAZINE MICROPARTICLES AND METHODS

CROSS-REFERENCE TO RELATED APPLICATIONS

The present application is a continuation of U.S. patent application Ser. No. 16/453,826, filed Jun. 26, 2019, which is a continuation of U.S. patent application Ser. No. 16/151,678, filed Oct. 4, 2018, now patented as U.S. Pat. No. 10,376,587, which is a divisional of U.S. application Ser. No. 15/152,355, filed May 11, 2016, now patented as U.S. Pat. No. 10,130,709, which is a divisional of U.S. application Ser. No. 14/127,158, filed Dec. 31, 2013, now patented as U.S. Pat. No. 9,364,436 which is a 371 of PCT/US2012/042998, filed Jun. 18, 2012, which claims benefit to U.S. Provisional Application No. 61/498,476, filed Jun. 17, 2011, the contents of which are incorporated herein by reference in their entirety.

TECHNICAL FIELD

Disclosed herein are diketopiperazine microparticles having high capacity for carrying and delivering a pharmaceutical substance. In particular, the microparticles comprise fumaryl diketopiperazine (FDKP) which can be used as a pulmonary drug delivery system for the treatment of disease or disorders requiring large doses of drugs or active agents, for example, to treat disease and disorders, including those of systemic or endocrine origin, including, pain, diabetes and obesity.

BACKGROUND

Delivery of drugs has been a major problem for many years, particularly when the compound to be delivered is unstable under the conditions encountered in the gastrointestinal tract when administered orally to a subject, prior to reaching its targeted location. For example, it is preferable in many cases to administer drugs orally, especially in terms of ease of administration, patient compliance, and decreased cost. However, many compounds, including small organic molecules, peptides and proteins are ineffective or exhibit low or variable potency when administered orally. Presumably, this is because the drugs are unstable to conditions in the digestive tract or because they are inefficiently absorbed.

Due to the problems associated with oral drug delivery, drug delivery to the lungs has been explored. For example, typically, drugs delivered to the lungs are designed to have an effect on the tissue of the lungs, for example, vasodilators, surfactants, chemotherapeutic agents or vaccines for flu or other respiratory illnesses. Other drugs, including nucleotide drugs, have been delivered to the lungs because they represent a tissue particularly appropriate for treatment, for example, for genetic therapy in cystic fibrosis, where retroviral vectors expressing a defective adenosine deaminase are administered to the lungs in an attempt to correct the defective gene.

Drug delivery to the lungs for agents having systemic effects can also be performed. Advantages of the lungs for delivery of systemic agents include the large surface area and the ease of uptake by the lung's mucosal surface. One problem associated with all of these forms of pulmonary drug delivery is that it is difficult to deliver drugs into the lungs due to problems in getting the drugs past all of the natural barriers, such as the cilia lining the trachea, and in trying to administer a uniform volume and weight of drug.

In addition, decreasing the amount of powder to be delivered to the lungs should be advantageous to the subject being treated so as to minimize coughing and prevent any loss of lung function, which can be a potential problem with increased amount of powders required to deliver an appropriate or increase in dose of an active agent. Accordingly, there is room for improvement in designing and providing pharmaceutical formulations requiring large amounts or doses of an active agent for pulmonary delivery to improve treatment and patience compliance.

SUMMARY

The present disclosure provides inhalation systems, microparticles and methods that allow for improved delivery of drugs to the lungs. Embodiments disclosed herein achieve improved delivery by providing diketopiperazine microparticles having high capacity for drug adsorption and yielding powders having high drug content. Powders made with the present microparticles can deliver increased drug content in lesser amounts of powder dose, which can facilitate drug delivery to a patient.

In one embodiment, the diketopiperazine microparticles herein are formed having a plurality of structural domains, each structural domain comprising a nucleus surrounded by layers of a porous crystalline material, wherein the nucleus or core comprises one to about 850 voxels as measured using X-ray tomography. In particular embodiments, the microparticles comprise on average more than 1,000 voxels per domain, or more than 2,000 voxels per domain. Each voxel comprises a defined cubic volume element measuring about 33 nm on each edge and contains a volume of about $3.6 \times 10^{-23}$ $m^3$. In some embodiments, diketopiperazine microparticles comprise one or more structural domains; each domain comprises about 2,000 voxels or more than 2,000 voxels; wherein the microparticles range in size from about 2,000 voxels to about 680,000 voxels for particles with a geometric size ranging from about 0.5 to about 4 µm. In this embodiment, the particles have a mass-weighted average particle size of about 33,000 voxels to about 216,000 voxels.

In another embodiment, a powder comprising microparticles of a diketopiperazine is provided; wherein the microparticles have a number-weighted average size ranging from about 500 voxels to about 125,000 voxels. In one embodiment, the number-weighted average particle size ranges from about 2,000 voxels to about 100,000 voxels; or from about 40,000 voxels to about 85,000 voxels.

In one embodiment, the high capacity particles are formed of 3,6-bis(N-fumaryl-4-aminobutyl)-2,5-diketopiperazine (fumaryl diketopiperazine) microparticles, FDKP and comprise a plurality of structural domains; wherein each particle comprises one or more structural domains. In this embodiment, a typical diketopiperazine microparticle for pulmonary delivery comprises from about 1 domain to about 1,000 domains; from 2 to about 800 domains; or from about 50 to about 250 domains. In particular embodiments, the number of domains per particle is on an average from about 3 to 160 domains, wherein the particles are from about 0.5 to 4 µm in geometric diameter.

In one embodiment, the FDKP microparticles comprise a number-weighted domain size average ranging from about 250 voxels to about 1370 voxels.

In some embodiments, high capacity FDKP microparticles comprise a voxel-weighted size distribution of domains with an average physical size ranging from about 300 nm to about 450 nm; or from about 310 nm to about 445 nm as measured by the radius of domain gyration.

In some embodiments, diketopiperazine microparticles comprise a drug or active agent, wherein said drug or active agent is a small organic molecule, peptide or protein. Examples of an endocrine hormone include, insulin, parathyroid hormone, calcitonin, glucagon, glucagon-like peptide 1, oxyntomodulin, oxytocin, CCK-8, PYY3-36, ghrelin and VIP (vasoactive intestinal peptide) an analog or active fragment of the endocrine hormone. Examples of small organic molecules include, a neurotransmitter agonist, a neurotransmitter antagonist, a pain inhibitory agent, including, morphine, and morphine derivatives, and triptans such as sumatriptan and rizatriptan, a vaccine, an anti-inflammatory agent, an anti-cancer agent, a cell receptor agonist molecule, or cell receptor antagonist molecule.

In another embodiment, a method of forming fumaryl diketopiperazine microparticles is provided, wherein the formed microparticles have a plurality of structural domains, each structural domain comprising a nucleus surrounded by layers of a porous crystalline material, and wherein the domain comprises more than 500 voxels as measured using X-ray tomography. The method comprises: providing a 2.75 wt % solution of a fumaryl diketopiperazine; feeding equal masses of about 11 wt % to about 12 wt % acetic acid and about 2.75 wt % fumaryl diketopiperazine solutions and containing a surfactant at a concentration of 0.05 wt % at a temperature of about 17° C. to about 22° C. through a high shear mixer, and collecting the fumaryl diketopiperazine microparticles. Some embodiments include a method of synthesizing fumaryl diketopiperazine microparticles comprising: collecting fumaryl diketopiperazine microparticles that are a product of feeding a precursor solution through a high shear mixer; wherein the precursor solution comprises a first solution comprising about 11 wt % to about 12 wt % acetic acid, a second solution comprising about 2.75 wt % fumaryl diketopiperazine, and the precursor solution comprises a surfactant at a concentration of about 0.05 wt %. In one embodiment, the surfactant used can be, for example, polysorbate 80. In certain embodiments, the method can further comprise the step of washing the suspension with deionized water to remove excess acid. In another embodiment, the method comprises adding a solution comprising an active ingredient, including a peptide or a small molecule to the microparticles in suspension and adjusting the pH of the solution to about 4.5 with an aqueous ammonia solution to promote adsorption of the active ingredient to the particles.

In another embodiment, a method of delivering an active agent to a patient with a disease or disorder is disclosed comprising: administering to a patient in need of treatment thereof a formulation comprising an active agent to treat the disease or disorder adsorbed to microparticles as described herein.

In one embodiment, the method of treatment is targeted for pulmonary delivery. In a particular embodiment, the method is for treating diabetes, comprising administering to a patient in need of treatment a dry powder formulation comprising insulin adsorbed to formed microparticles of a diketopiperazine, wherein the diketopiperazine is fumaryl diketopiperazine, and the microparticles have a plurality of structural domains, each structural domain comprising a nucleus surrounded by layers of a porous crystalline material, wherein the nucleus comprises more than 500 voxels as measured using X-ray tomography and the microparticles are delivered to the deep lung by inhalation of said dry powder formulation by the patient. In this and other embodiments, the formulation is used to deliver using a high resistance inhalation system.

In one embodiments, the diketopiperazine microparticles have a plurality of structural domains, each structural domain comprising a nucleus surrounded by layers of a porous crystalline material, wherein the nucleus comprises more than 500 voxels as measured using X-ray tomography. The diketopiperazine microparticles can have a specific surface area greater than 35 $m^2/g$. In certain embodiments, the diketopiperazine microparticles are provided having a high specific surface area greater than 70 $m^2/g$. In a particular embodiment, the microparticles formed of 3,6-bis(N-fumaryl-4-aminobutyl)-2,5-diketopiperazine (FDKP) have a specific surface area of about 72 $m^2/g$ to about 94 $m^2/g$. Microparticles having high specific surface area in the range from 72 $m^2/g$ to about 94 $m^2/g$ can exhibit characteristics beneficial to delivery to the lungs such as improved capacity for carrying a drug or active substance with improved drug adsorption and which maintain excellent aerodynamic performance. The particles also exhibit improved stability.

In another embodiment, the diketopiperazine microparticles are associated with a drug. In this embodiment, the drug is a peptide or protein, such as a hormone, including, insulin, parathyroid, glucagon, glucagon-like peptide 1, and the like. In another embodiment, the drug or active agent can be a drug targeted for local or systemic delivery, including small molecule such as a neurotransmitter, pain relief agents, vasoactive agents, immunosuppressing agents, anti-cancer agents, vaccines, nucleic acid molecules, and/or prophalactive agents. In certain embodiments, the drug to be delivered can comprise a triptan, including, sumatriptan, rizatriptan and salts thereof.

In a further embodiment, the diketopiperazine microparticles are 3,6-bis(N-fumaryl-4-aminobutyl)-2,5-diketopiperazine (fumaryl diketopiperazine) microparticles in a dry powder formulation for pulmonary delivery of drug or active agent for the treatment of disease and disorders; wherein the drug or active agent is adsorbed onto preformed particles. The amount of drug to be adsorbed by the microparticles depends on the drug to be formulated.

In some embodiments, the diketopiperazine microparticles comprise a peptide such as insulin, wherein the insulin content, for example, for microparticle made with FDKP, is greater than 4 U/mg. In a particular embodiment, the FDKP microparticles can comprise 6 U/mg of insulin or greater amounts of insulin per mg of powder formulation. In this embodiment, the FDKP microparticles containing about 5 U/mg of insulin have a specific surface area ranging from about 28 $m^2/g$ to about 71 $m^2/g$, and FDKP microparticles containing about 6 U/mg of insulin have, for example, specific surface area ranging from about 19 $m^2/g$ to about 57 $m^2/g$.

Further embodiments concern drug delivery systems comprising an inhaler, a unit dose dry powder medicament container, and a powder comprising the microparticles disclosed herein and an active agent.

Another embodiment disclosed herein includes a method of delivering insulin to a patient in need thereof comprising administering a dry powder comprising diketopiperazine microparticles disclosed herein to the deep lung by inhalation of the dry powder by the patient. In aspects of this embodiment, particular features of an inhaler system are specified.

In various embodiments of the FDKP microparticles, the drug can be, for example, a peptide, including, insulin, glucagon-like peptide-1 (GLP-1), glucagon, exendin, parathyroid hormone, calcitonin, oxyntomodulin, and the like. In another embodiment of the FDKP microparticles, the peptide content can vary depending on downstream processing conditions. In a particular example, the FDKP microparticles can be prepared to have drug/peptide content that can vary depending on the dose to be targeted or delivered. For example, wherein the drug is insulin, the insulin component can be greater than 4 U/mg in the powder formulation to decrease powder content to be delivered to a patient.

Further embodiments concern drug delivery systems comprising an inhaler, a unit dose dry powder medicament container, for example, a cartridge, and a powder comprising the microparticles disclosed herein and an active agent. In one embodiment, the delivery system for use with the dry powders includes an inhalation system comprising a high resistance inhaler having air conduits which impart a high resistance to airflow through the conduits for deagglomerating and dispensing the powder. In one embodiment, the inhalation system has a resistance value of, for example, approximately 0.065 to about 0.200 $(\sqrt{kPa})$/liter per minute. In certain embodiments, the dry powders can be delivered effectively by inhalation with an inhalation system wherein the peak inhalation pressure differential can range from about 2 to about 20 kPa, which can produce resultant peak flow rates of about between 7 and 70 liters per minute. In certain embodiments, the inhalation system are configured to provide a single dose by discharging powder from the inhaler as a continuous flow, or as one or more pulses of powder delivered to a patient. In some embodiments disclosed herewith, the dry powder inhaler system comprises a predetermined mass flow balance within the inhaler. For example, a flow balance of approximately 10% to 70% of the total flow exiting the inhaler and into the patient is delivered by one or more dispensing ports, which airflow passes through the area containing the powder formulation, and wherein approximately 30% to 90% air flow is generated from other conduits of the inhaler. Moreover, bypass flow, or flow not entering and exiting the area of powder containment such as through a cartridge, can recombine with the flow exiting the powder dispensing port within the inhaler to dilute, accelerate and ultimately deagglomerate the fluidized powder prior to exiting the mouthpiece. In one embodiment, flow rates ranging from about 7 to 70 liters per minute result in greater than 75% of the container or the cartridge contents dispensed in fill masses between 1 and 30 mg. In certain embodiments, an inhalation system as described above can emit a respirable fraction/fill of a powder dose at percentages greater than 40% greater than 50%, greater than 60%, or greater than 70% and may be up to about 90%, 95%, 99%, or may be nearly 100% in a single inhalation.

In particular embodiments, an inhalation system is provided comprising a dry powder inhaler, a dry powder formulation comprising microparticles of fumaryl diketopiperazine, wherein the FDKP microparticles have a plurality of structural domains, each structural domain comprising a nucleus surrounded by layers of a porous crystalline material, wherein the domain comprises more than 500 voxels as measured using X-ray tomography. In some aspects of this embodiment of the inhalation system, the dry powder formulation is provided in a unit dose cartridge for using with a reusable inhaler. Alternatively, the dry powder formulation can be preloaded in a single use, disposable inhaler. In this embodiment, the structural configuration of the inhalation system allows the deagglomeration mechanism of the inhaler to produce respirable fractions greater than 50%; that is, more than half of the powder contained in the inhaler (cartridge) is emitted as particles of less than 5.8 μm. The inhalers can discharge greater than 85% of a powder medicament contained within a container during dosing. In certain embodiments, the inhalers can discharge greater than 85% of a powder medicament contained in a single inhalation. In one embodiment, the inhalers can discharge greater than about 90%, or about 97% to nearly 100% of the cartridge contents or container contents in less than 3 seconds at pressure differentials between 2 and 5 kPa with fill masses ranging up to 30 mg or greater.

In specific embodiments, methods of synthesizing FDKP microparticles having a plurality of structural domains are described, each structural domain comprising a domain surrounded by layers of a porous crystalline material, wherein the domain comprises more than 500 voxels as measured using X-ray tomography. The methods comprise feeding equal masses of about 11 wt % acetic acid to about 12 wt % and about 2.75 wt % FDKP solutions at about 17° C. to about 22° C. through a high shear mixer, such as a Dual-feed SONOLATOR™ at 2000 psi through a 0.001-in$^2$ orifice to form a suspension. The methods can further comprise the step of precipitating the microparticles out of solution and collecting the microparticles formed in a deionized water reservoir of about equal mass and temperature. In certain embodiments, the method further comprises concentrating the microparticle suspension by washing the microparticles in, for example, deionized water using a tangential flow filtration technique. In this and other embodiments, the precipitate can be first concentrated to about 4% solids then further washed with deionized water. In some embodiments, the suspension typically can be concentrated to about 10% solids based on the initial mass of FDKP composition used. The concentrated suspension can be assayed for solids content by an oven drying method. In embodiments disclosed herein, the method further comprises determining the surface area of the particles after the particles are dried.

In specific embodiments, methods of making diketopiperazine microparticles having a plurality of structural domains are described, each structural domain comprising a nucleus surrounded by layers of a porous crystalline material, wherein the domain comprises more than 500 voxels as measured using X-ray tomography, utilizes a diketopiperazine having the formula 3,6-bis(N-X-4-aminobutyl)-2,5-diketopiperazine, wherein X is selected from the group consisting of fumaryl, succinyl, maleyl, and glutaryl. In an exemplary embodiment, the diketopiperazine has the formula 3,6-bis(N-fumaryl-4-aminobutyl)-2,5-diketopiperazine, or 3,6-bis(N-fumaryl-4-amino-butyl)-2,5-diketopiperazine.

Another embodiment disclosed herein includes a method for making a dry powder formulation comprising FDKP microparticles having a plurality of structural domains, each structural domain comprising a nucleus surrounded by layers of a porous crystalline material, wherein the domain comprises more than 500 voxels as measured using X-ray tomography, and a drug or active agent; wherein the microparticles range in size from about 2,000 voxels to about 680,000 voxels and have a mass-weighted average particle size of about 33,000 voxels to about 216,000 voxels. In one embodiment, microparticles can have an average size ranging from about 500 voxels to about 125,000 voxels; about 2,000 voxels to about 100,000 voxels; about 50,000 voxels to about 80,000 voxels; about 60,000 voxels to about 70,000 voxels; or about 60,000 voxels to about 65,000 voxels In this embodiment, the method comprises adding a solution comprising the active agent, such as a small molecule, including a triptan, or a peptide including, insulin, glucagon, glucagon-like peptide-1, oxyntomodulin, peptide YY(3-36), ghrelin, vasoactive intestinal peptide, oxytocin, CCK, and the like to the microparticle suspension; adding aqueous ammonia to the suspension to raise the pH of the suspension to 4.5; and flash-freezing the resultant suspension in liquid nitrogen and lyophilizing pellets formed to produce a dry powder comprising the FDKP microparticles.

Further embodiments involve methods of treating an insulin-related disorder comprising administering a dry powder described above to a person in need thereof. In various embodiments, an insulin-related disorder can specifically include or exclude any or all of pre-diabetes, type 1 diabetes mellitus (honeymoon phase, post-honeymoon phase, or both), type 2 diabetes mellitus, gestational diabetes, hypoglycemia, hyperglycemia, insulin resistance, secretory dysfunction, impaired early-phase release of insulin, loss of pancreatic β-cell function, loss of pancreatic β-cells, and metabolic disorder.

In one embodiment, a method of treating a disease or disorder is disclosed, including, treating an endocrine-related disease or disorder comprising administering to a person in need thereof a dry powder formulation comprising FDKP microparticles having a plurality of structural domains, each structural domain comprising a nucleus surrounded by layers of a porous crystalline material, wherein the domain comprises more than 500 voxels as measured using X-ray tomography and a drug suitable to treat said disease or disorder; wherein the microparticles range in size from about 2,000 voxels to about 400,000 voxels and have a mass-weighted average particle size of about 33,000 voxels to about 216,000 voxels. In one embodiment, microparticles can have an average size ranging from about 500 voxels to about 125,000 voxels; from 2,000 voxels to 100,000 or from 50,000 voxels to 80,000 voxels One embodiment includes a method of treating an insulin-related disorder comprising administering a dry powder comprising microparticles of FDKP described above to a person in need thereof. In various embodiments, an insulin-related disorder can specifically include or exclude any or all of pre-diabetes, type 1 diabetes mellitus (honeymoon phase, post-honeymoon phase, or both), type 2 diabetes mellitus, gestational diabetes, hypoglycemia, hyperglycemia, insulin resistance, secretory dysfunction, impaired early-phase release of insulin, loss of pancreatic β-cell function, loss of pancreatic β-cells, and metabolic disorder. In one embodiment, the dry powder comprises insulin. In other embodiments, the dry powder comprises glucagon, an exendin, or GLP-1.

BRIEF DESCRIPTION OF THE DRAWINGS

The following drawings form part of the present specification and are included to further demonstrate certain aspects of the examples disclosed herein. The disclosure may be better understood by reference to one or more of these drawings in combination with the detailed description of specific embodiments presented herein.

FIGS. 1A and 1B depict graphic representations of number-weighted size distributions of particles generated from data collected from X-Ray tomography studies of high capacity particles (FIG. 1A) compared to particles generated by a standard prior art method (FIG. 1B).

FIGS. 2A and 2B depict graphic representations of voxel-weighted size distributions of particles generated from data collected from X-Ray tomography studies of high capacity particles (FIG. 2A) compared to particles generated by a standard prior art method (FIG. 2B).

FIGS. 3A and 3B depict graphic representations of number-weighted size distributions of domains generated from data collected from X-Ray tomography studies of high capacity particles (FIG. 3A) compared to particles generated by a standard prior art method (FIG. 3B).

FIGS. 4A and 4B depict graphic representations of voxel-weighted size distributions of domains generated from data collected from X-Ray tomography studies of high capacity particles (FIG. 4A) compared to particles generated by a standard prior art method (FIG. 4B).

FIG. 5A depicts a graph of voxel-weighted distribution of physical domain size for high capacity FDKP microparticles compared to standard prior art FDKP microparticles (FIG. 5B) calculated by radius of gyration. FIG. 5C is an overlay of the high capacity microparticles (solid line) and prior art particles (broken lines) showing the differences between the high capacity particles and standard particles size distribution.

DETAILED DESCRIPTION

Figure 6:
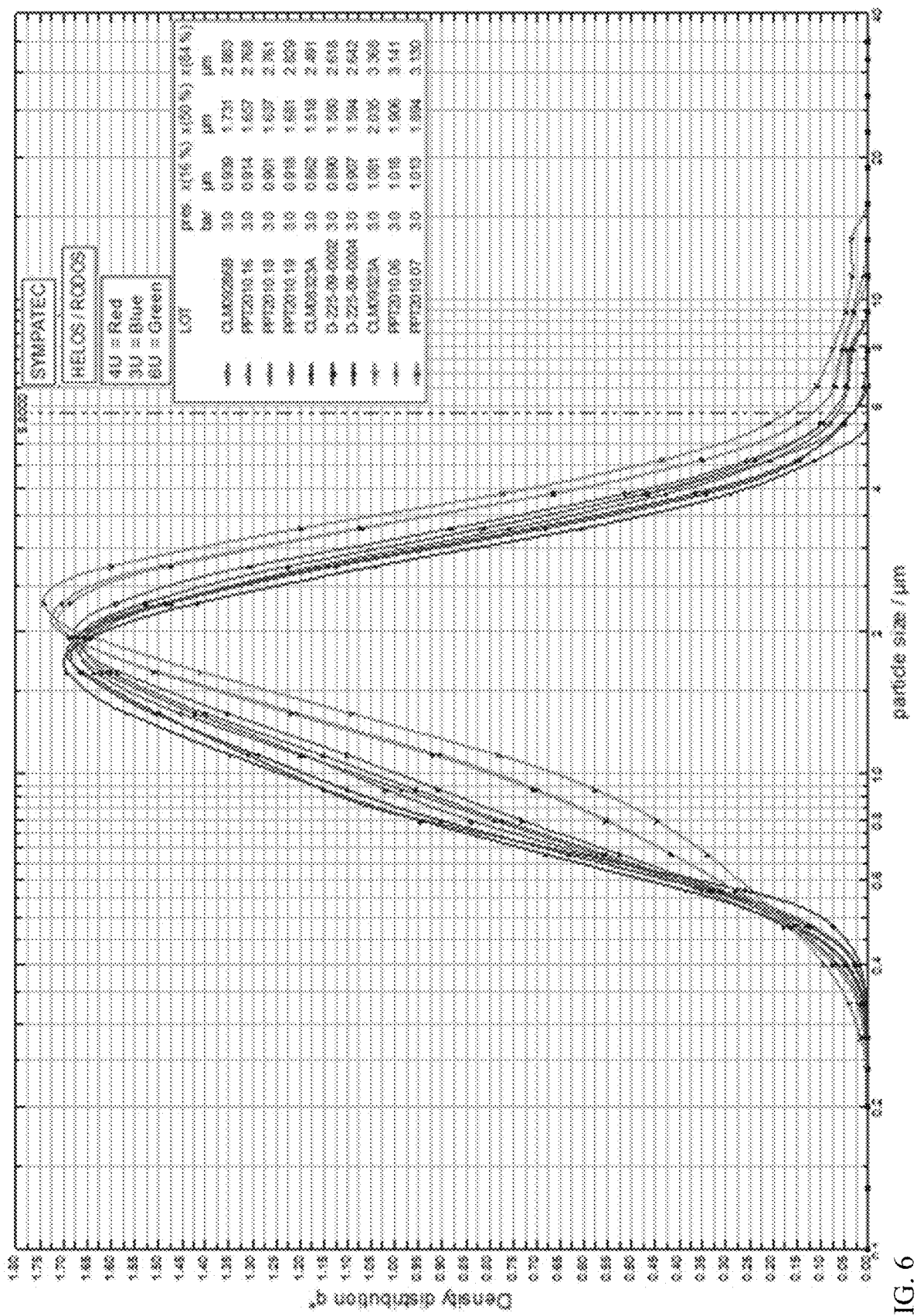
FIG. 6 depicts a graph of geometric particle size distribution for bulk powders with different insulin content for standard FDKP microparticles 3 U/mg and 4 U/mg and high capacity FDKP microparticles containing 6 U/mg.

As stated, drug delivery to the lungs offers many advantages. However, it is difficult to deliver drugs into the lungs, due to problems in transporting the drugs past natural physical barriers in a uniform volume and weight of the drug. Disclosed herein are diketopiperazine microparticles as drug delivery agents, having a high capacity for adsorbing an active agent including, small molecules, nucleic acids and peptides. In one embodiment, the microparticles have a specific surface area of greater than about 70 m$^2$/g. Methods of making the microparticles and methods of using the microparticles are disclosed. In an exemplary embodiment, the present microparticles can deliver peptides for pulmonary inhalation, for example, insulin in concentrations greater than 4 IU/mg. In some embodiments, a microparticle may comprise about 18% to about 25%, about 20% to about 25%, or about 21% to about 25% insulin by weight.

As used herein, the term "microparticle" refers to a particle with a diameter of about 0.5 to about 1000 μm, irrespective of the precise exterior or interior structure. Microparticles having a diameter of less than 10 microns can reach the lungs, successfully passing most of the natural barriers. A diameter of less than about 10 microns is required to navigate the turn of the throat. To reach the deep lung (or alveolar region) where most efficient absorption is believed to occur, it is preferred to maximize the proportion of particles contained in the "respirable fraction" (RF), generally accepted to be those particles with an aerodynamic diameter less than 5.8 microns, though some references use somewhat different ranges, as measured using standard techniques, for example, with an Andersen Cascade Impactor. Other impactors can be used to measure aerodynamic particle size such as the NEXT GENERATION IMPACTOR™ (NGI™, MSP Corporation), for which the respirable fraction is defined by similar aerodynamic size, for example<6.4 μm. In some embodiments, a laser diffraction apparatus is used to determine particle size, for example, the laser diffraction apparatus disclosed in U.S. patent application Ser. No. 12/727,179, filed on Mar. 18, 2010, which is incorporated herein in its entirety for its relevant teachings, wherein the volumetric median geometric diameter (VMGD) of the particles is measured to assess performance of the inhalation system. For example, in various embodiments cartridge emptying of ≥80%, 85%, or 90% and a VMGD of the emitted particles of ≤12.5 μm, ≤7.0 μm, or ≤4.8 μm can indicate progressively better aerodynamic performance. Embodiments disclosed herein show FDKP microparticles having a plurality of structural domains, each structural domain comprising a nucleus surrounded by layers of a porous crystalline material, wherein the domain comprises more than 500 voxels as measured using X-ray tomography. In certain embodiments, FDKP microparticles described herein have a specific surface area greater than 36 $m^2/g$ or greater than 70 $m^2/g$ and exhibit characteristics beneficial to delivery of drugs to the lungs, including maintaining improved aerodynamic performance.

Respirable fraction on fill (RF/fill) represents the fraction or percentage of powder in a dose that is emitted from an inhaler upon discharge of the powder content filled for use as the dose, and that is suitable for respiration, i.e., the percent of particles from the filled dose that are emitted with sizes suitable for pulmonary delivery, which is a measure of microparticle aerodynamic performance. As described herein, a RF/fill value of 40% or greater than 40% reflects acceptable aerodynamic performance characteristics. In certain embodiments disclosed herein, the respirable fraction on fill can be greater than 50%. In an exemplary embodiment, a respirable fraction on fill can be up to about 80%, wherein about 80% of the fill is emitted with particle sizes<5.8 μm as measured using standard techniques.

As used herein, the term "dry powder" refers to a fine particulate composition that is not suspended or dissolved in a propellant, carrier, or other liquid. It is not meant to necessarily imply a complete absence of all water molecules.

It should be understood that specific RF/fill values can depend on the inhaler used to deliver the powder. Powders generally tend to agglomerate and crystalline DKP microparticles form particularly cohesive powders. One of the functions of a dry powder inhaler is to deagglomerate the powder so that the resultant particles comprise a respirable fraction suitable for delivering a dose by inhalation. However, deagglomeration of cohesive powders is typically incomplete so that the particle size distribution seen when measuring the respirable fraction as delivered by an inhaler will not match the size distribution of the primary particles, that is, the profile will be shifted toward larger particles. Inhaler designs vary in their efficiency of deagglomeration and thus the absolute value of RF/fill observed using different designs will also vary.

As used herein, the term "about" is used to indicate that a value includes the standard deviation of the measurement for the device or method being employed to determine the value.

As used herein, the term voxel is a unit of measure used in X-ray tomography to define a volume element. The contents of each voxel are represented by absorbances that are proportional to the linear absorption coefficients (LAC) of the material in each volume element. The linear absorbance coefficient for water is approximately 0.1 $μm^{-1}$ (3.3× $10^{-3}$/voxel). A voxel is defined as a cubic volume element measuring about 33 nm on each side or edge and contains a volume of about $3.6×10^{-23}$ $m^3$.

Diketopiperazines

As used herein, diketopiperazines include substituted or diketopiperazines and related compounds. One class of drug delivery agents that has been used to overcome problems in the pharmaceutical arts such as drug instability and/or poor absorption are the 2,5-diketopiperazines. 2,5-Diketopiperazines are represented by the compound of the general Formula 1 as shown below wherein $E_1$ and $E_2$ are independently N or more particularly NH. In other embodiments, $E_1$ and/or $E_2$ are independently an oxygen or a nitrogen so that wherein either one of the substituents for $E_1$ and $E_2$ is an oxygen and the other is a nitrogen the formula yields the substitution analog diketomorpholine, or when both $E_1$ and $E_2$ are oxygen the formula yields the substitution analog diketodioxane.

Formula 1

$$\begin{array}{c} R_2 \\ \diagdown \\ \end{array} \begin{array}{c} E_1 \\ \end{array} \begin{array}{c} O \\ \diagup \\ \end{array}$$
$$\begin{array}{c} O \\ \diagup \\ \end{array} \begin{array}{c} E_2 \\ \end{array} \begin{array}{c} R_1 \\ \diagdown \\ \end{array}$$

These 2,5 diketopiperazines have been shown to be useful in drug delivery, particularly those bearing acidic $R_1$ and $R_2$ groups as described in, for example, U.S. Pat. No. 5,352,461 entitled "Self Assembling Diketopiperazine Drug Delivery System;" U.S. Pat. No. 5,503,852 entitled "Method For Making Self-Assembling Diketopiperazine Drug Delivery System;" U.S. Pat. No. 6,071,497 entitled "Microparticles For Lung Delivery Comprising Diketopiperazine;" and U.S. Pat. No. 6,331,318 entitled "Carbon-Substituted Diketopiperazine Delivery System," each of which is incorporated herein by reference in its entirety for all that it teaches regarding diketopiperazines and diketopiperazine-mediated drug delivery. In some embodiments, a 2,5-diketopiperazine may be 3,6-di(4-aminobutyl)-2,5-diketopiperazine, 3,6-di(succinyl-4-aminobutyl)-2,5-diketopiperazine, 3,6-di(maleyl-4-aminobutyl)-2,5-diketopiperazine, 3,6-di(citraconyl-4-aminobutyl)-2,5-diketopiperazine, 3,6-di(glutaryl-4-aminobutyl)-2,5-diketopiperazine, 3,6-di(malonyl-4-aminobutyl)-2,5-diketopiperazine, 3,6-di(oxalyl-4-aminobutyl)-2,5-diketopiperazine, ro 3,6-di(fumaryl-4-aminobutyl)-2,5-diketopiperazine.

Diketopiperazines can be formed into microparticles that incorporate a drug or microparticles onto which a drug can be adsorbed. The combination of a drug and a diketopiperazine can impart improved drug stability and/or absorption characteristics. These microparticles can be administered by various routes of administration. As dry powders these microparticles can be delivered by inhalation to specific areas of the respiratory system, including the lungs.

Such microparticles are typically obtained by pH-based precipitation of the free acid (or base) resulting in self-assembled microparticles comprising aggregated crystalline plates. The stability of the particle can be enhanced by small amounts of a surfactant, such as polysorbate-80, in the DKP solution from which the particles are precipitated (see for example US Patent Publication No. 2007/0059373 entitled "Method of drug formulation based on increasing the affinity of crystalline microparticle surfaces for active agents" which is incorporated herein by reference in its entirety for all that it teaches regarding the formation and loading of DKP microparticles and dry powders thereof). Ultimately solvent can be removed to obtain a dry powder. Appropriate methods of solvent removal include lyophilization and spray drying (see for example US Patent Publication No. 2007/0196503 entitled "A method for improving the pharmaceutic properties of microparticles comprising diketopiperazine and an active agent" and U.S. Pat. No. 6,444,226 entitled "Purification and stabilization of peptide and protein pharmaceutical agents" each of which is incorporated herein by reference in its entirety for all that it teaches regarding the formation and loading of DKP microparticles and dry powders thereof). The microparticles disclosed herein are distinct from microparticles composed of DKP salts. Such particles are typically formed (as opposed to dried) by spray drying, resulting in spheres and/or collapsed spheres of an amorphous salt (as opposed to a free acid or base) so that they are chemically, physically, and morphologically distinct entities. The present disclosure refers to FDKP to be understood as the free acid or the dissolved anion.

Methods for synthesizing diketopiperazines are described in, for example, Katchalski, et al., J. Amer. Chem. Soc. 68, 879-880 (1946) and Kopple, et al., J. Org. Chem. 33(2), 862-864 (1968), the teachings of which are incorporated herein by reference in their entirety. 2,5-Diketo-3,6-di(aminobutyl)piperazine (Katchalski et al. refer to this as lysine anhydride) can also be prepared via cyclodimerization of N-ε-P-L-lysine in molten phenol, similar to the Kopple method, followed by removal of the blocking (P)-groups with an appropriate reagent and conditions. For example, CBz-protecting groups can be removed using 4.3 M HBr in acetic acid. This route can be preferred because it uses a commercially available starting material, it involves reaction conditions that are reported to preserve stereochemistry of the starting materials in the product and all steps can be easily scaled up for manufacture. Methods for synthesizing diketopiperazines are also described in U.S. Pat. No. 7,709,639, entitled, "Catalysis of Diketopiperazine Synthesis," which is also incorporated by reference herein for its teachings regarding the same.

Fumaryl diketopiperazine (3,6-bis(N-fumaryl-4-aminobutyl)-2,5-diketo-diketopiperazine; FDKP) is one preferred diketopiperazine for pulmonary applications:

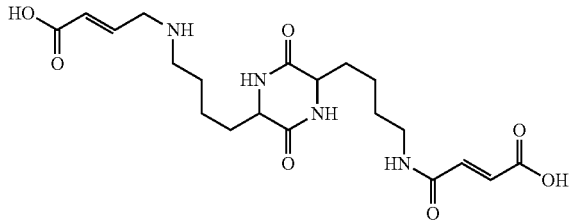 [SMILES: O=C(O)/C=C/CNCCCCC1NC(=O)C(CCCCNC(=O)/C=C/C(=O)O)NC1=O]

FDKP provides a beneficial microparticle matrix because it has low solubility in acid but is readily soluble at neutral or basic pH. These properties allow FDKP to crystallize and the crystals to self-assemble to form microparticles under acidic conditions. The particles dissolve readily under physiological conditions where the pH is neutral. As noted, microparticles having a diameter of between about 0.5 and about 10 microns can reach the lungs, successfully passing most of the natural barriers. Particles in this size range can be readily prepared from FDKP.

As described above, microparticles having a diameter of about 0.5 and about 10 microns can reach the lungs, successfully passing most of the natural barriers. Particles in this size range can be readily prepared from diketopiperazines with acidic groups, such as the carboxylate groups in FDKP (as well as in related molecules such as 3,6-di(4-X-aminobutyl)-2,5-diketopiperazine wherein X is succinyl, glutaryl, or maleyl). Upon acid precipitation self-assembled particles composed of aggregates of crystalline plates are obtained. The structure and size of these plates can be controlled by reaction conditions during synthesis of the microparticles and therefore, can relate to the specific surface area of the particles which in turn is implicated in effects on the structure, loading capacity, and aerodynamic performance of the particles.

The SSA of DKP microparticles is a measure of average crystal size and can be used to gauge the relative contributions of crystal nucleation and growth to microparticle characteristics. SSA depends on the size of microparticle crystals and the density (ρ) of the microparticle matrix and is inversely proportional to the characteristic size, L, of the crystals. Embodiments disclosed herein show that microparticles with a specific surface area greater than 36 $m^2/g$ exhibit characteristics even more beneficial than standard microparticle for the delivery of drugs to the lungs such as improved aerodynamic performance with moderately efficient inhalers such as the MEDTONE® inhaler disclosed in U.S. Pat. No. 7,464,706 entitled, "Unit Dose Cartridge and Dry Powder Inhaler," which is incorporated by reference herein for its teachings regarding the same. In some embodiments, the diketopiperazine microparticles can have a specific surface area greater than about 70 $m^2/g$ and can increased aerodynamic performance and improved drug adsorption capacity.

In one embodiment, the diketopiperazine microparticles herein are formed having a plurality of structural domains, each structural domain comprising a nucleus surrounded by layers of a porous crystalline material, wherein the domain or core comprises more than 500 voxels as measured using X-ray tomography. In particular embodiments, the microparticles comprise more than 1,000 voxels per domain, or more than 2,000 voxels per domain as the median number. In some embodiments, diketopiperazine microparticles comprise one or more cores comprising about 2,000 voxels, or more than 2,000 voxels; wherein the microparticles range in size from about 2,000 voxels to about 680,000 voxels and have a mass-weighted average particle size of about 33,000 to about 216,000 voxels. In one embodiment, microparticles can have an average size ranging from about 500 voxels to about 125,000 voxels; about 2,000 voxels to about 100,000 voxels, about 50,000 voxels to about, 80,000 voxels, about 60,000 voxels to about 70,000 voxels, or about 60,000 voxels to about 65,000 voxels. In a particular embodiment the average particle size as a measure of mass, or mass-weighted average particle size is about 62,000 to 63,000 voxels. In some embodiments microparticles may have a voxel-weighted particle size of about 50,000 voxels to about 200,000 voxels, about 75,000 voxels to about 150,000 voxels, about 100,000 to about 150,000 voxels, or about 120,000 voxels to about 130,000 voxels.

In an exemplary embodiment, the FDKP microparticles comprise a plurality of structural domains, each structural domain comprising a domain or core surrounded by layers of a porous crystalline material, wherein the domain comprises more than 500 voxels as measured using X-ray tomography and each particle is greater than 2,000 voxels. In this and other embodiments, the particles can vary in number of domains. In some embodiments, a microparticle and each domain can vary in size. In some embodiments, each domain can have a number-weighted average size in the range of about 250 voxels to about 1400 voxel, about 500 voxels about 1000 voxels, about 700 voxels to about 900 voxels, about 800 voxels about 900 voxels, about 800 voxels to about 850 voxels, or about 810 voxels to about 820 voxels. In this and other embodiments, each domain can have a voxel-weighted size of about 500 to about 2,000 voxels, about 800 voxels to about 1500 voxels, about 900 voxels to about 1300 voxels, about 1000 voxels to about 1300 voxels, about 1100 voxels to about 1200 voxels, or about 1150 voxels to about 1200 voxels.

In embodiments described herewith, the microparticles can have a plurality of structural domains. In some embodiments, the microparticles for pulmonary delivery can comprise from 1 to about 1000 structural domains.

In another embodiment, a powder comprising microparticles of a diketopiperazine is provided; wherein the microparticles have a number-weighted average size ranging from about 500 voxels to about 125,000 voxels. In one embodiment, the number-weighted average particle size ranges about 2,000 voxels to 100,000 voxels; about 40,000 voxels to about 85,000 voxels; about 60,000 voxels to about 70,000 voxels, or about 60,000 voxels to about 65,000 voxels.

In one embodiment, high capacity particles of a diketopiperazine are provided, comprising a plurality of structural domains; wherein each particle comprises one or more structural domains. In this embodiment, a typical diketopiperazine microparticle comprises from about 1 to about 1000 domains and each domain range in size from about 250 to about 2,000 voxels; from about 500 to about 1800 voxels, or from about 500 voxels to about 1,800 voxels. In this embodiment, the number of domains per particle is on an average from about 75 to 80 domains, wherein the particles are from about 0.5 µm to 4 µm. In some embodiments microparticles may have a voxel-weighted average domain size of about 300 nm to about 400 nm, about 350 nm to about 400 nm, or about 370 nm to about 390 nm.

To form FDKP microparticles with an active agent, for example, insulin for making formulations to treat diabetes, insulin-loaded FDKP microparticles, insulin can be adsorbed directly onto the microparticles while the microparticles are in suspension (i.e., prior to freeze drying) by adding an insulin stock solution to the FDKP microparticle suspension. In one embodiment, a pH control step can also be performed after the addition of the insulin stock solution. This step can promote insulin adsorption onto the microparticles in suspension prior to further processing. Increasing the pH of the suspension to about 4.5 promotes complete insulin adsorption onto the microparticles in suspension without excessive dissolution of the FDKP from the particle matrix and also improves the stability of insulin in the bulk drug product. The suspension can be flash-frozen drop-wise (i.e., cryo-pelletized) in liquid nitrogen and lyophilized to remove the solvent and obtain a dry powder. In alternative embodiments the suspension can be spray-dried to obtain the dry powder.

A manufacturing process for making the FDKP microparticles containing insulin is provided. In this embodiment, using a high shear mixer such as a DUAL-FEED SONOLATOR™ at 2000 psi through a 0.001-in$^2$ orifice, or for example, the high shear mixer as disclosed in U.S. patent application Ser. No. 12/917,611 (US 2011/0105719, filed on Nov. 2, 2010, which disclosures are incorporated herein by reference in their entirety, equal masses of about 10.5 wt % acetic acid and about 2.5 wt % FDKP solutions at about 16° C.±about 2° C. (Table 1 and 2) can be fed at 2000 psi through a 0.001 in$^2$ orifice. The precipitate can be collected in a deionized (DI) water reservoir of about equal mass and temperature. The resultant suspension comprises about 0.8% solids. The precipitate can be concentrated and washed by tangential flow filtration. The precipitate can be first concentrated to about 4% solids then washed with deionized water. The suspension can be finally concentrated to about 10% solids based on the initial mass of FDKP. The concentrated suspension can be assayed for solids content by an oven drying method.

Selection and Incorporation of Active Agents

As long as the microparticles described herein retain the required specific surface area greater than 36 m$^2$/g, they can adopt other additional characteristics beneficial for delivery to the lung and/or drug adsorption. U.S. Pat. No. 6,428,771 entitled "Method for Drug Delivery to the Pulmonary System" describes DKP particle delivery to the lung and is incorporated by reference herein for its teachings regarding the same. U.S. Pat. No. 6,444,226, entitled, "Purification and Stabilization of Peptide and Protein Pharmaceutical Agents" describes beneficial methods for adsorbing drugs onto microparticle surfaces and is also incorporated by reference herein for its teachings regarding the same. Microparticle surface properties can be manipulated to achieve desired characteristics as described in U.S. Pat. No. 7,799,344, entitled "Method of Drug Formulation based on Increasing the Affinity of Crystalline Microparticle Surfaces for Active Agents" which is incorporated by reference herein for its teachings regarding the same. U.S. Pat. No. 7,803,404 entitled "Method of Drug Formation based on Increasing the Affinity of Active Agents for Crystalline Microparticle Surfaces" describes methods for promoting adsorption of active agents onto microparticles. U.S. Pat. No. 7,803,404 is also incorporated by reference herein for its teachings regarding the same.

The microparticles described herein can comprise one or more active agents. As used herein "active agent", used interchangeably with "drug", refers to pharmaceutical substances, including small molecule pharmaceuticals, biologicals and bioactive agents. Active agents can be naturally occurring, recombinant or of synthetic origin, including proteins, polypeptides, peptides, nucleic acids, organic macromolecules, synthetic organic compounds, polysaccharides and other sugars, fatty acids, and lipids, and antibodies and fragments thereof, including, but not limited to, humanized or chimeric antibodies, F(ab), F(ab)$_2$, a single-chain antibody alone or fused to other polypeptides or therapeutic or diagnostic monoclonal antibodies to cancer antigens. The active agents can fall under a variety of biological activity and classes, such as vasoactive agents, neuroactive agents, hormones, anticoagulants, immunomodulating agents, cytotoxic agents, antibiotics, antiviral agents, antigens, infectious agents, inflammatory mediators, hormones, and cell surface antigens. More particularly, active agents can include, in a non-limiting manner, cytokines, lipokines, enkephalins, alkynes, cyclosporins, anti-IL-8 antibodies, IL-8 antagonists including ABX-IL-8; prostaglandins including PG-12, LTB receptor blockers including LY29311, BIIL 284 and CP105696; triptans such as sumatriptan and palmitoleate, insulin and analogs thereof, growth hormone and analogs thereof, parathyroid hormone (PTH) and analogs thereof, parathyroid hormone related peptide (PTHrP), oxytocin, leuprolide, interferon-alpha, RGD peptide, DDAVP peptide, GHR peptide, detirelex human growth hormone, albumin, immunoglobulin G, cyclosporine, ghrelin, obestatin, enterostatin, granulocyte macrophage colony stimulating factor (GM-CSF), granulocyte colony stimulating factor (GCSF), amylin, amylin analogs, glucagon-like peptide 1 (GLP-1), clopidogrel, PPACK (D-phenylalanyl-L-prolyl-L-arginine chloromethyl ketone), oxyntomodulin (OXM), peptide YY(3-36) (PYY), adiponectin, cholecystokinin (CCK), secretin, gastrin, glucagon, motilin, somatostatin, brain natriuretic peptide (BNP), atrial natriuretic peptide (ANP), IGF-1, growth hormone releasing factor (GHRF), integrin beta-4 precursor (ITB4) receptor antagonist, nociceptin, nocistatin, orphanin FQ2, calcitonin, CGRP, angiotensin, substance P, neurokinin A, pancreatic polypeptide, neuropeptide Y, delta-sleep-inducing peptide and vasoactive intestinal peptide.

In certain embodiments, the drug content of the particles can vary depending on the form and size of the drug to be delivered. The range of loading of the drug to be delivered is typically between about 0.01% and about 20%, about 25%, or greater, depending on the form and size of the drug to be delivered. For insulin, preferred loads can be greater than 15%, about 18% to about 25%, about 20% to about 25%, or about 21% to about 25%. In specific embodiments, insulin can be loaded to FDKP microparticles in amounts greater than 4 U/mg of dry powder formulation for pulmonary delivery. In some embodiments, the insulin content of the present FDKP microparticles can be 5 U/mg, 6 U/mg or greater in a dry powder formulation for inhalation. In a specific embodiment, a dose of insulin that can be administered to a patient can be about 60 U or higher in a single inhalation, using the inhalation system described herein.

EXAMPLES

The following examples are included to demonstrate embodiments of the disclosed microparticles. It should be appreciated by those of skill in the art that the techniques disclosed in the examples which follow represent techniques discovered by the inventor to function well in the practice of the present disclosure, and thus can be considered to constitute preferred modes for its practice. However, those of ordinary skill in the art should, in light of the present disclosure, appreciate that many changes can be made in the specific embodiments which are disclosed and still obtain a like or similar result.

Example 1

Manufacturing Procedures For Making Standard FDKP Microparticles With and Without Insulin The first step in the manufacture of FDKP microparticles is the formation of the microparticles by pH-induced crystallization of FDKP and the self-assembly of the FDKP crystals into microparticles having an overall spherical morphology. Accordingly, the manufacture of microparticles is essentially a crystallization process. Excess solvent can be removed by washing the suspension by repeated centrifugation, decantation and re-suspension, or by diafiltration. An example of a standard method for synthezing FDKP microparticles is described above and in International PCT Patent Application No. PCT/US2010/038298 (WO 2010/144789), which disclosure is incorporated herein by reference in its entirety.

Microparticles were manufactured from FDKP and insulin. FDKP was dissolved in aqueous $NH_4OH$ to form a solution. A feed stream of this solution was combined with a feed stream of an aqueous HOAc solution in a high shear mixer to form an aqueous suspension of microparticles.

The FDKP feed solution was prepared with about 2.5 wt % FDKP, about 1.6 wt % concentrated $NH_4OH$ (about 28 to about 30 wt % $NH_3$) and about 0.05 wt % polysorbate 80. The acetic acid feed solution was prepared at about 10.5 wt % glacial acetic acid and about 0.05 wt % polysorbate 80. Both feed solutions were filtered through an about 0.2 μm membrane prior to use.

Equal amounts (by mass) of each feed solution were pumped through a DUAL-FEED SONOLATOR™ equipped with the #5 orifice (0.0011 sq. inch). The minor pump was set to 50% for equal flow rates of each feed stream and the feed pressure was about 2000 psi. The receiving vessel contained DI water equal to the mass of either feed solution (e.g. 4 kg FDKP feed solution and 4 kg HOAc feed solution would be pumped through the SONOLATOR™ into the receiving vessel containing 4 kg of DI water).

The resulting suspension was concentrated and washed by means of tangential flow filtration using a 0.2 m² PES membrane. The suspensions were first concentrated to about 4% solids then diafiltered with DI water and finally concentrated to about 16% nominal solids. The actual percent solids of the washed suspension was determined by "loss on drying." Alternative methods can be used to measure the percent solids in a suspension such as the one disclosed in PCT Patent Application No. PCT/US2011/035112 (WO 2011/140175), filed on May 4, 2011, entitled, Determining Percent Solids in Suspension Using Raman Spectroscopy, which disclosure is incorporated herein by reference for its teachings.

Insulin stock solutions were prepared containing about 10 wt % insulin (as received) in a solvent comprising about 2 wt % HOAc in DI water, and sterile filtered. Based on the solids content of the suspension, the appropriate amount of stock solution was added to the mixed suspension. The resulting microparticle/insulin was then adjusted from a pH of about 3.6 to a pH of about 4.5 using an ammonia solution.

The suspension comprising FDKP microparticles containing insulin was transferred to a cryogranulator/pelletizer, for example, as disclosed in U.S. patent application Ser. No. 12/917,623 (US 2011/0100028), which disclosure is incorporated herein by reference as the teaching pertain herein, and flash frozen in liquid nitrogen. The ice pellets were lyophilized to produce a dry powder.

B. High Capacity FDKP Microparticle Formation

Microparticles of FDKP were prepared similarly as described in A and in WO 201/144789, under two sets of conditions (Table 1).

TABLE 1

| Particle formation conditions | | | | | | |
|---|---|---|---|---|---|---|
| | Feed solution 1 (wt %) | | | Feed solution 2 (wt %) | | |
| Condition | FDKP | NH₄OH | PS80 | HOAc | PS80 | T (° C.) |
| 1 | 2.5 | 1.6 | 0.05 | 10.5 | 0.05 | 16 |
| 2 | 2.75 | 1.52 | 0.05 | 11.55 | 0.05 | 22 |

Standard FDKP microparticles were made using standard conditions as shown in Table 1, Condition 1. Exemplary high capacity FDKP microparticles, Condition 2, were prepared similarly as condition 1, using two feed solutions in a manufacturing process using as shown in Table 1. In Condition 2, the manufacturing processes comprises the steps of feeding equal masses of about 11.5 wt % acetic acid and about 2.75 wt % FDKP solutions at temperature of 22° C. through a high shear mixer (Dual-feed SONOLATOR™) at 2000 psi through a 0.001-in² orifice to form a suspension. FDKP microparticles precipitate out of solution and the microparticles formed are collected in a deionized water reservoir of about equal mass and temperature. The particles are rinsed to remove excess acid, dried and samples of the powder were analyzed by X-ray tomography.

Standard and high capacity particles were characterized by X-ray tomography. The three-dimensional representations of the particles are discretized into cubic volume elements 33 nm on each side. Volume elements are called voxels, named by analogy with pixels for picture elements. The contents of each voxel are represented by absorbances that are proportional to the linear absorption coefficients (LAC) of the material in each volume element. The linear absorbance coefficient for water is approximately 0.1 $\mu m^{-1}$ ($3.3 \times 10^{-3}$/voxel) and the calculated linear absorption coefficient for an FDKP crystal with a density of 1.4 g/cm$^3$ is 1.3 $\mu m^{-1}$ ($43 \times 10^{-3}$/voxel).

Particles were identified by first excluding any voxel with LAC<$14 \times 10^{-3}$/voxel (corresponding to approximately 33% FDKP solids). Starting with any remaining voxel, adjacent voxels with LAC≥$14 \times 10^{-3}$/voxel were added. Voxels adjacent to these voxels were then added in turn until all contiguous voxels had been incorporated into the particle. The process was repeated with other voxels to define subsequent particles.

The particle structure was interpreted as a collection of adjacent domains consisting of "cores" and "shells." Cores consist of contiguous voxels in a region where the voxel density (LAC) is a local maximum while the shells are the voxels of lower density surrounding the cores. Only particles containing more than one "core" and at least 2000 voxels were included in the analysis.

FIGS. 1A and 1B depict graphic representation of number-weighted size distributions of particles generated from data collected from X-ray tomography studies of high capacity particles (FIG. 1A) compared to particles generated by a standard prior art method (FIG. 1B). The data illustrate the high capacity particles have a number-weighted average size of 62,347 voxels with a standard deviation of 62,702 voxels compared to standard particles having an average size of 108,135 with a standard deviation of 140,444 voxels, almost twice as large as the high capacity particles.

The particles were also characterized in terms of their envelope density. The envelope surrounding a particle is a convex shell that completely encloses the particles. The solids fraction of each envelope was calculated by dividing the size of the particle (volume of voxels making up the particle) by the volume of the envelope. FIGS. 2A and 2B illustrate data obtained and analyzed for correlation of this particle characteristics, wherein FIG. 2B depicts the results of microparticles prepared using standard conditions Condition 1 and FIG. 2A illustrates data resulting from microparticles prepared using Condition 2. The results show that the high capacity particles are more compact or less concave than the standard particles. Additionally, the data illustrate that the high capacity microparticles measured are about one half to one third smaller than standard, prior art microparticles by volume as measured by X-ray tomography procedures. The present microparticles also have about one quarter fewer domains per particles as compared to the standard particles.

FIGS. 2A and 2B depict graphic representations of voxel/mass-weighted size distributions of particles generated from data collected from X-ray tomography studies of high capacity particles (FIG. 2A) compared to particles generated by a standard prior art method (FIG. 2B). The data illustrates the standard particles (FIG. 1B) are larger on average than the high capacity particles (FIG. 1A) whether the distribution is number-weighted, or mass (voxel)-weighted (FIGS. 2A and 2B).

Table 2 and FIGS. 3A and 3B depict graphic representations of number-weighted size distributions of domains generated from data collected from X-ray tomography studies of high capacity FDKP particles (FIG. 3A) compared to FDKP particles generated by a standard prior art method (FIG. 3B). FIGS. 4A and 4B depict graphic representations of mass (voxel)-weighted size distributions of domains generated from data collected from X-Ray tomography studies of high capacity FDKP particles (FIG. 4A) compared to FDKP particles generated by a standard prior art method (FIG. 4B). The representative data in FIGS. 3A and 4A also indicate that the high capacity particles are smaller because 1) the domains that constitute the high capacity particles are smaller than those in standard particles (FIGS. 3B and 4B), and 2) fewer domains make up the high capacity particles (Table 2). In a comparison of equal-sized particles, e.g., particles 2 $\mu$m in diameter, the high capacity particle would comprise approximately 158 domains with an average size of 780 voxels while the standard particle would comprise approximately 112 domains with an average size of 1050 voxels.

TABLE 2

Comparison of HC and standard particles

| Property | High Capacity FDKP | Standard FDKP | Ratio of means |
|---|---|---|---|
| Particles Size (mean ± std dev) | N = 54 | N = 65 | |
| Number-weighted | 62,347 ± 62,702 | 108,135 ± 140,444 | 0.577 |
| Voxel-weighted | 124,238 ± 90,875 | 287,734 ± 181,427 | 0.590 |
| Domains Size (mean ± std dev) | N = 4151 | N = 6665 | |
| Number-weighted | 811 ± 555 | 1055 ± 811 | 0.769 |
| Voxel-weighted | 1191 ± 683 | 1677 ± 1098 | 0.710 |
| Number of domains per particle (mean ± std dev) | 77 ± 74 | 103 ± 132 | 0.748 |

Both types of FDKP particles were also characterized in terms of their radius of gyration. The radius of gyration, $R_g = (R^2_g)^{1/2}$, is a measure of the physical size of the domain. For a sample population of particles, each domain was calculated using the following formula:

$$R_g^2 = \sum (x_i - x_c)^2 + (y_i - y_c)^2 + (y_i - y_c)^2 + \frac{1}{4}c^2$$

where ($x_i$, $y_i$, $z_i$) is the center of voxel i, ($x_c$, $y_c$, $z_c$) is the centroid of the domain and c is the size of the voxel (33 nm). FIGS. 5A, 5B and 5C are graphic representations of the data obtained from the high capacity particles (5A) and standard particles (5B). The domains of the high capacity particles are smaller on average (378 nm) and have a distribution of average sizes, ranging from 312 nm to 444 nm, which is narrower than those of the standard particles. The domains for the standard particles have an average size of 426 nm and have an average size distribution ranging from 340 nm to 512 nm. This suggests that the balance between nucleation and growth lies closer to nucleation for the high capacity particles than for standard particles.

Example 2

Geometric Particle Size Analysis of Emitted Formulations by Volumetric Median Geometric Diameter (VMGD) Characterization Laser diffraction of dry powder formulations emitted from dry powder inhalers is a common methodology employed to characterize the level of de-agglomeration subjected to a powder. The methodology indicates a measure of geometric size rather than aerodynamic size as provided in industry standard impaction methodologies. Typically, the geometric size of the emitted powder includes a volumetric distribution characterized by the median particle size, VMGD. Importantly, geometric sizes of the emitted particles are discerned with heightened resolution as compared to the aerodynamic sizes provided by impaction methods. Smaller sizes are preferred and result in greater likelihood of individual particles being delivered to the pulmonary tract. Thus, differences in inhaler de-agglomeration and ultimate performance can be easier to resolve with diffraction. In these experiments, inhalers were tested with laser diffraction at pressures analogous to actual patient inspiratory capacities to determine the effectiveness of the inhalation system to de-agglomerate powder formulations. Specifically, the formulations included cohesive diketopiperazine powders with an active insulin loaded ingredient and without. FDKP microparticles prepared using Condition 1 were loaded with an insulin content of 3 U/mg and 4 U/mg (maximal capacity for insulin without losing aerodynamic performance for pulmonary delivery), and FDKP microparticles prepared using Condition 2 were also prepared and tested. Reported in FIG. 6 is a graphic representation of VMGD for the various powders tested using a dry powder inhaler as described in U.S. patent application Ser. No. 12/484,129 (US 2009/0308391)

FIG. 6 depicts a graph representative of geometric particle size distribution for bulk powders with different insulin content for standard FDKP microparticles 3 U/mg and 4 U/mg (maximal) and high capacity FDKP microparticles containing 6 U/mg. The data in FIG. 6 indicates that the microparticles having an insulin content of 6 U/mg exhibit a slight increase in VMGD, however, the increase in VMGD did not change performance of pulmonary delivery over the 3 U/mg or 4 U/mg powders. This is evidence in Table 3 in which the powders were administered to healthy normal volunteers in a clinical trial.

TABLE 3

Fine particle dose and insulin AUC

| | 20 U | | 40 U | | 60 U | |
|---|---|---|---|---|---|---|
| | FPD (U) | AUC (μU · min/mL) | FPD (U) | AUC (μU · min/mL) | FPD (U) | AUC (μU · min/mL) |
| 3 U/mg | 12.6 | 4408 | — | — | — | — |
| 4 U/mg | 13.9 | 5236 | 23.6 | 7886 | — | — |
| 6 U/mg | 13.2 | 4234 | 22.9 | 6844 | 32.7 | 9997 |

The data illustrates that the 6 U/mg FDKP/insulin powder formulation prepared using Condition 2 performed effectively to deliver a larger dose of insulin than the standard particles (3 U/mg and 4 U/mg) as measured by fine particle dose (FPD) and area under the curve (AUC) at various doses. The high capacity particles can also be used to deliver smaller doses of an active, for example, insulin and therefore, less powder to a patient.

The data demonstrate that the particles prepared under condition 2 exhibit a significantly higher capacity to adsorb insulin from solution than particles prepared under Condition 1.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a" and "an" and "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

The use of the term "or" in the claims is used to mean "and/or" unless explicitly indicated to refer to alternatives only or the alternatives are mutually exclusive, although the disclosure supports a definition that refers to only alternatives and "and/or."

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Of course, variations on those preferred embodiments will become apparent to those of ordinary skill in the art upon reading the foregoing description. The inventor expects those of ordinary skill in the art to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above cited references and printed publications are herein individually incorporated by reference in their entirety.

Further, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A drug deliverable agent for pulmonary inhalation for treating disease, the drug deliverable agent comprising:
    diketopiperazine microparticles; wherein said diketopiperazine microparticles comprise
        a specific surface area greater than about 70 m²/g,
        a mass-weighted average particle size of about 33,000 to about 216,000 voxels measured by X-ray tomography for particle size measuring about 0.5 µm to about 4 µm in geometric diameter,
        a plurality of structural domains having one or more cores surrounded by layers of a porous crystalline material, and
        a concentration of an active ingredient, or analog thereof, of about 18% to about 25% by weight of said microparticle.

2. The drug deliverable agent of claim 1, wherein said diketopiperazine microparticles comprise a voxel-weighted average domain size of about 300 nm to about 400 nm.

3. The drug deliverable agent of claim 1, wherein said diketopiperazine is fumaryl diketopiperazine (3,6-bis(N-fumaryl-4-aminobutyl)-2,5-diketopiperazine; or salt thereof.

4. The drug deliverable agent of claim 1, wherein said active ingredient is a small organic molecule.

5. The drug deliverable agent of claim 1, wherein said active ingredient is a neurotransmitter, pain relief agent, vasoactive agent, immunosuppressing agent, anti-cancer agent, vaccine, nucleic acid molecule or prophalactive agent.

6. The drug deliverable agent of claim 1, wherein said active ingredient is a triptan selected from sumatriptan, rizatriptan and salts thereof.

7. The drug deliverable agent of claim 1, wherein said active ingredient is a peptide wherein the peptide is insulin, glucagon, glucagon-like peptide-1, oxyntomodulin, peptide YY(3-36), ghrelin, vasoactive intestinal peptide, oxytocin or CCK.

8. The drug deliverable agent of claim 1, wherein said active ingredient is insulin.

9. The drug deliverable agent of claim 8, wherein said fumaryl diketopiperazine comprises an insulin content greater than about 4 U/mg.

10. The drug deliverable agent of claim 1, wherein the diketopiperazine microparticles comprise structural domains ranging in number-weighted size from about 250 voxels to about 1,400 voxels.

11. The drug deliverable agent of claim 1, wherein the diketopiperazine microparticles comprise structural domains ranging in voxel-weighted size from about 500 voxels to about 2,000 voxels.

12. The drug deliverable agent of claim 1, wherein the plurality of structural domains have an average size from about 300 nm to about 450 nm as measured by radius of gyration.

13. The drug deliverable agent of claim 1, further comprising a surfactant.

14. The drug deliverable agent of claim 13, wherein the surfactant is polysorbate 80.

15. The drug deliverable agent of claim 1, wherein the deliverable agent is in an inhalable dry powder form.

16. The drug deliverable agent of claim 15, wherein the deliverable agent is capable of delivery to a patient in a single inhalation to the deep lung using a dry powder inhaler.

* * * * *